(12) United States Patent  (10) Patent No.: US 8,249,895 B2
Faulkner et al.  (45) Date of Patent: Aug. 21, 2012

(54) ELECTRONIC HEALTH RECORD SYSTEM UTILIZING DISPARATE RECORD SOURCES

(75) Inventors: Judith R. Faulkner, Madison, WI (US);
Carl D. Dvorak, Verona, WI (US);
Brian M. Weisberger, Madison, WI (US); Janet L. Campbell, Madison, WI (US); Timothy W. Escher, Lodi, WI (US); Dustin L. Gage, Madison, WI (US); Sean Conrad, Madison, WI (US); Bhavik Shah, Madison, WI (US); Michael J. Kantor, Madison, WI (US); Matthew D. Sidney, Fitchburg, WI (US)

(73) Assignee: Epic Systems Corporation, Verona, WI (US)

( * ) Notice: Subject to any disclaimer, the term of this patent is extended or adjusted under 35 U.S.C. 154(b) by 272 days.

(21) Appl. No.: 12/391,120

(22) Filed: Feb. 23, 2009

(65) Prior Publication Data
US 2009/0228303 A1 Sep. 10, 2009

Related U.S. Application Data

(60) Provisional application No. 61/030,734, filed on Feb. 22, 2008.

(51) Int. Cl.
*G06Q 50/00* (2012.01)
(52) U.S. Cl. .................................. 705/3; 705/2
(58) Field of Classification Search .......... 705/2, 3, 705/8, 51, 555; 715/733; 707/770; 726/27
See application file for complete search history.

(56) References Cited

U.S. PATENT DOCUMENTS

| | | | |
|---|---|---|---|
| 5,959,621 A * | 9/1999 | Nawaz et al. ............... | 715/733 |
| 6,988,075 B1 * | 1/2006 | Hacker ....................... | 705/3 |
| 7,275,220 B2 | 9/2007 | Brummel et al. | |
| 7,337,123 B2 * | 2/2008 | Dvorak et al. ............. | 705/7.19 |
| 7,428,494 B2 * | 9/2008 | Hasan et al. ................ | 705/3 |
| 7,542,911 B2 * | 6/2009 | Barret et al. ............... | 705/2 |
| 7,555,436 B2 * | 6/2009 | Brown ........................ | 705/2 |
| 7,647,320 B2 * | 1/2010 | Mok et al. .................. | 707/770 |
| 2002/0120472 A1 | 8/2002 | Dvorak et al. | |
| 2003/0115084 A1 * | 6/2003 | Gage ........................... | 705/3 |
| 2003/0208381 A1 | 11/2003 | Walter et al. | |
| 2004/0010425 A1 * | 1/2004 | Wilkes et al. ............... | 705/3 |
| 2004/0078236 A1 * | 4/2004 | Stoodley et al. ............ | 705/2 |
| 2004/0215981 A1 * | 10/2004 | Ricciardi et al. ........... | 713/202 |
| 2005/0038670 A1 * | 2/2005 | Takkar et al. ............... | 705/2 |
| 2005/0159984 A1 * | 7/2005 | Hirano et al. .............. | 705/3 |
| 2005/0165627 A1 * | 7/2005 | Fotsch et al. .............. | 705/3 |
| 2005/0171818 A1 * | 8/2005 | McLaughlin ............... | 705/3 |
| 2005/0234741 A1 * | 10/2005 | Rana et al. ................. | 705/2 |
| 2005/0251423 A1 | 11/2005 | Bellam et al. | |
| 2006/0117021 A1 | 6/2006 | Sidney et al. | |
| 2006/0143050 A1 * | 6/2006 | Dean .......................... | 705/3 |
| 2006/0178910 A1 * | 8/2006 | Eisenberger et al. ....... | 705/3 |
| 2006/0259324 A1 * | 11/2006 | Patterson .................... | 705/2 |
| 2007/0016450 A1 * | 1/2007 | Bhora et al. ................ | 705/3 |

(Continued)

*Primary Examiner* — Gerald J. O'Connor
*Assistant Examiner* — Jonathan K Ng
(74) *Attorney, Agent, or Firm* — Boyle Fredrickson, S.C.

(57) ABSTRACT

A system for facilitating patient ownership of his or her medical data through the use of third-party health repositories that preserves the maximum information content of the medical records by displaying information relevant to the authority of the medical data as reflected by its source and types of modification as it has moved between institutions, as well as the data itself. In this way, improved use of this data is made possible.

17 Claims, 3 Drawing Sheets

U.S. PATENT DOCUMENTS

| | | | |
|---|---|---|---|
| 2007/0192137 A1* | 8/2007 | Ombrellaro | 705/2 |
| 2007/0198296 A1* | 8/2007 | Pellinat et al. | 705/2 |
| 2008/0033761 A1 | 2/2008 | Brummel et al. | |
| 2008/0097786 A1* | 4/2008 | Sachdeva | 705/2 |
| 2008/0109361 A1* | 5/2008 | Urali et al. | 705/51 |
| 2008/0140577 A1* | 6/2008 | Rahman et al. | 705/71 |
| 2008/0172737 A1* | 7/2008 | Shen et al. | 726/21 |
| 2009/0150292 A1* | 6/2009 | Trinh et al. | 705/55 |

* cited by examiner

ELECTRONIC HEALTH RECORD SYSTEM UTILIZING DISPARATE RECORD SOURCES

CROSS-REFERENCE TO RELATED APPLICATIONS

This application claims the benefit of U.S. provisional application 61/030,734 filed Feb. 22, 2008 hereby incorporated by reference.

STATEMENT REGARDING FEDERALLY SPONSORED RESEARCH OR DEVELOPMENT

Background of the Invention

The present invention relates to electronic medical records and, in particular, to an electronic medical record system providing improved integration of portable medical records.

Electronic medical records offer a number of advantages over conventional paper-based recordkeeping. First, the cost of generating, storing, and accessing electronic medical records is potentially much lower than for comparable paper- or document-based record systems. Electronic medical records are more resistant to loss or damage and, with the increased availability of computer devices with display and networking capability, the speed and convenience of accessing electronic medical records is far superior to their paper counterparts. Electronic medical records facilitate the collection of all relevant information for a particular patient in a single system, giving healthcare providers a more complete view of the patient's health. Because electronic medical records are machine-readable, they may be analyzed with programs to assess the efficacy of particular courses of treatment, to provide automatic notices or devise theories, and to otherwise automate the process of delivering high-quality health care services.

Electronic medical records also promise to improve the patient's access to his or her own records and thus beneficially increase patient involvement in the healthcare process. Healthcare providers having electronic medical record systems may provide Web portals to their patients allowing protected access by the patient to selected healthcare information. One such system is the MyChart™ healthcare portal commercially available from Epic Systems Corporation of Verona, Wis. Such healthcare portal systems should be distinguished from healthcare websites which allow the patient to record healthcare information but do not provide patient access to clinical medical records collected by healthcare professionals.

A third benefit to electronic medical records is that they are easily transported, for example on optical or digital media or over the Internet, and in this way can provide continuity in a patient's medical history as the patient moves among institutions. Toward this end, a number of organizations both within and outside of the healthcare industry (such as Google and Microsoft) have taken steps toward creating health data repositories that might serve to hold electronic medical records in the standard formats under the control of a patient. These data repositories foresee the possibility that patients will become the custodians of their own medical records in alignment with U.S. law giving patients ownership of their medical record data.

SUMMARY OF THE INVENTION

The present inventors have recognized that the benefits of a patient controlling his or her medical records can be at odds with the patient's desire that the physician have authoritative medical data on which the physician may rely. While a patient's characterizations of his or her medical condition is an important element in obtaining a complete picture of the patient's health, patient-edited data or data that is corrupted or materially redacted can be confusing or misleading, a fact that may lead physicians to give this data very little weight.

The promise of health record portability from third-party record repositories may fall far short of expectations if patient-stored and -transported health records are ignored by physicians or treated as no better than a patient health history questionnaire currently filled out by patients when moving to a new physician or medical practice.

The present invention addresses this problem by generating and preserving additional data related to the authority of transferred medical records. This authority information may be displayed to the physician concurrently with the display of the underlying medical data allowing the physician to better assess and thus more fully use data that has been transferred from other sources. In this respect, the present invention may distinguish among physician-generated data having the highest authority, patient-collected data (entrusted to the patient by another institution) having various levels of authority depending on the degree of editing and redaction of the data and patient-generated data having lesser authority for some types of data. In different embodiments, the value of the data is further enhanced by displaying the source of the data (e.g. a particular hospital or institution collecting the data) and the extent to which the data may omit important elements.

In this context, "physician-generated" data will mean clinical medical data generated by the physician or other health care professional working with the physician, "patient-collected" data will mean clinical medical data entrusted to the patient and being transferred under the authority or control of the patient, while "patient-generated" data will mean medical information developed by the patient using the patient's own observations or memory. "Patient-generated" and "patient-collected" data will sometimes be referred to collectively as "patient-controlled" medical data.

Specifically then, the present invention provides a health record system integrating a first and second clinical record system associated with different medical institutions and the medical record repository. The first clinical record system, associated with the first medical institution, provides at least one computer communicating with a set of data terminals and a first database executing a first stored program to collect, organize, and display physician-generated medical data for given patients. The first clinical record system includes an authentication protocol limiting access by non-healthcare professionals. The medical record repository likewise provides at least one computer communicating with a set of data terminals and a repository database and executing a repository stored program to collect, organize, and display medical data controlled by given patients. The medical record repository includes an authentication protocol limiting access by others than the given patients.

In the invention, the repository program of the medical record repository operates to:

(a) accept into the repository database patient-generated medical data from a given patient;

(b) accept into the repository database patient-collected medical data from a second clinical record system of a second medical institution in a manner to be separately identified from the patient-generated data; and (c) respond to authorization by the given patient to transmit at least some of the patient-generated data and patient-collected data to the first clinical record system.

Using information from the medical record repository, the first stored program of the first clinical record system further operates to provide a display output providing medical data for the given patient visually linked to an indication of an authority of the data based on its identification as physician-generated, patient-generated, or patient-collected.

It is thus a feature of at least one embodiment of the invention to provide not only medical data but also to indicate the authority of the data improving the ability of the physician to use data from other sources.

The repository program further stores an identification of the second medical institution which may be displayed by the first program.

It is thus a feature of at least one embodiment of the invention to provide the physician with the ability to both judge medical data based on its specific source and to permit rehabilitation of data that may have lost its authority, the rehabilitation being done by the physician contacting the original source.

The medical data may have a data type related to a medical character of the data and independent of a source of the data and the first stored program may further operate to display physician-generated, patient-generated and patient-collected data sorted according to data types, so that similar data types are proximate to each other in the display.

It is thus a feature of at least one embodiment of the invention to allow visual integration of data from multiple sources in the display by data type, making the data more accessible to a physician, without obscuring the underlying authority of the data.

The repository program may accept health record documents from the second health institution comprised of multiple elements of medical data and may allow the given patient to selectively authorize a subset of the medical data of the document for transmission to the first clinical record system. The repository program may separately identify medical data associated with a document in which some medical data was not authorized for transmission to the first clinical record system from medical data associated with a document in which all medical data was authorized for transmission to the first clinical record system.

It is thus a feature of at least one embodiment of the invention to provide an indication to the physician that there may have been material omissions in a transferred medical record, lowering its authority, even though the included portions of the medical record are of high authority.

The repository program may allow editing of the patient-collected medical data by the given patient and the repository program may identify such edited medical data in a manner to be separately identified from medical data unedited by the given patient.

It is thus a feature of at least one embodiment of the invention to indicate that clinical medical data may have been edited or changed by the patient, thus implicitly lowering its authority.

Patient-collected data edited by the given patient may be identified as patient-generated data by the repository program.

It is thus a feature of at least one embodiment of the invention to provide a simple method of categorizing the authority of edited clinical data.

The repository program may accept health record documents of medical data from the second health institution and evaluate a digital signature or watermark in the documents, or the quality of a secure channel used to transfer the document, or other technological authentication system to ensure the documents have not been edited after release by the second health institution before identifying them as patient-collected data. As used herein, document shall refer to a collection of medical data received from a clinical institution presenting a cohesive view of the patient's health information and subject to a common authentication mechanism.

It is thus a feature of at least one embodiment of the invention to permit the use of clinical data transferred under the custody of the patient without necessarily degrading its authority. The watermarking process allows control of the files to be transferred while ensuring their integrity.

Alternatively, the repository program may communicate electronically directly with the second health institution to obtain patient-collected data.

It is thus an object of the invention to provide a system of transfer of clinical data without loss of authority using a trusted third-party intermediary.

The repository program may further communicate with the first program to provide a display output of the physician-generated data for the given patient to the patient using the repository program.

It is thus a feature of at least one embodiment of the invention to provide a mechanism allowing the patients to view their clinical records in combination with the management of clinical records from multiple sources.

The second program may further operate to:

accept into the repository database patient-collected medical data from the first clinical record system in a manner to be separately identified from the patient-generated data; and respond to authorization by the given patient to transmit at least some of the patient-generated data and patient-collected data to the second clinical record system.

It is thus a feature of at least one embodiment of the invention to provide a conduit for medical data between multiple institutions currently providing patient care.

The repository program may further operate to respond to authorization by the given patient to transmit at least some of the patient-generated data to the second clinical record system.

It is thus an object of the invention to provide a simple mechanism for a patient to update records at multiple institutions These particular features and advantages may apply to only some embodiments falling within the claims and thus do not define the scope of the invention.

DETAILED DESCRIPTION OF THE PREFERRED EMBODIMENT

Figure 1:
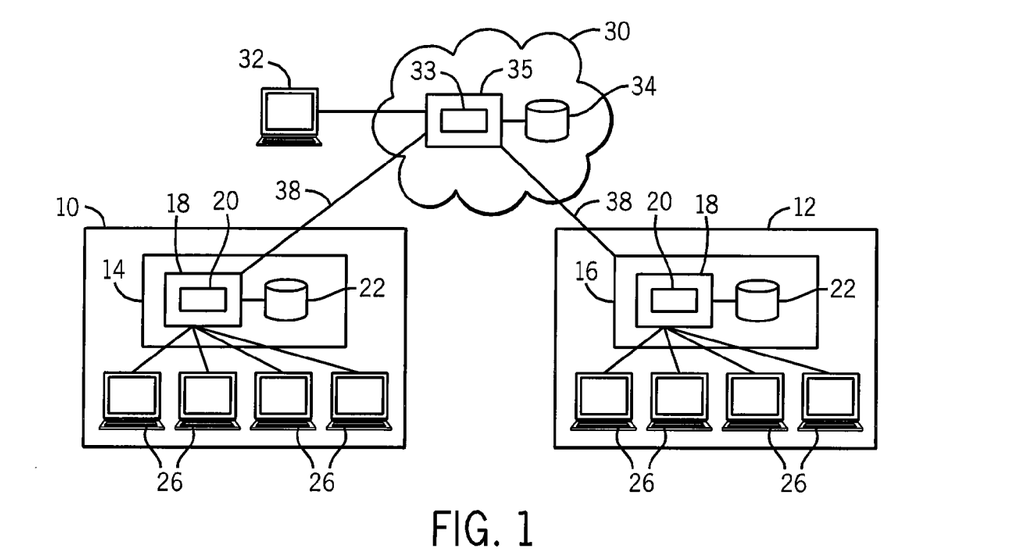
FIG. 1 is a graphical representation of the transfer of clinical medical data between a first and second clinical institution via a health data repository serving to link the two.

Referring now to FIG. 1, first and second clinical institutions 10 and 12, such as hospitals or clinics or the like, may provide for electronic medical records systems 14 and 16 respectively. As is generally understood in the art, medical record systems 14 and 16 may store, organize, and display clinical medical data for patients. As used herein, clinical medical data refers to medical information based on direct observation of patients by healthcare professionals.

The electronic medical record systems 14 and 16 may employ one or more electronic computers 18 executing stored programs 20 to implement a database 22 holding the clinical medical records as well as the other features are of the electronic medical record system. Multiple terminals 26 may communicate with the computer 18 through a local area network or via the Internet to allow access to the medical records by healthcare professionals of the institutions 10 and 12. This access is controlled by an authorization protocol implemented by the programs 20 to limit access by non-healthcare professionals, for example, through the use of a password/username combination or other well-known authentication techniques. This limitation of access may admit to multiple permission levels allowing some access, for example, selective read access by the patients for their own records. Generally, the records within the databases 22 are subject to the recordkeeping requirements and regulations of the Health Insurance Portability and Accountability Act (HIPAA). These clinical records will be termed physician-generated, recognizing that they may be developed by a broad class of healthcare professionals including but not limited to physicians.

Electronic medical record systems 14 and 16 suitable for this purpose are commercially available from Epic Systems Corporation and are described by multiple published U.S. pending applications assigned to Epic Systems Corporation including: 2008/0033761 "System and method for a seamless user interface for an integrated electronic health care information system"; 2007/0143149 "Data tagging and report customization method and apparatus"; 2006/0080620 "Electronic system for collecting and automatically populating clinical order information in an acute care setting"; 2003/0220815 "System and method of automatically determining and displaying tasks to healthcare providers in a care-giving setting"; 2003/0216945 "Method for analyzing orders and automatically reacting to them with appropriate responses"; 2003/0208391 "Rules based ticketing for self-scheduling of appointments"; 2003/0208381 "Patient health record access system"; 2003/0139943 "Healthcare information system with clinical information exchange"; 2003/0130872 "Methods and apparatus for managing and using inpatient healthcare information"; 2003/0061073 "Method and system for displaying patient information"; 2002/0120472 "System and method for integration of health care records"; 2002/0083075 "System and method for a seamless user interface for an integrated electronic health care information system"; and 2002/0080189 "Electronic system for collecting and communicating clinical order information in an acute care setting" all hereby incorporated by reference.

Referring still to FIG. 1, a given patient may record and access patient-generated medical information by means of a health data repository 30, for example, accessible over the Internet by the patient using a home data terminal 32.

In this regard, the health data repository 30 may use one or more computers 35 executing a stored program 33 to implement a database 34 used to hold the patient-generated medical records as well as implement other features of the health data repository 30 to be described. The home data terminal 32 may, for example, use a browser program to connect with a Web server implemented by the stored program 33 of the health data repository 30. Typically, the patient may use the home data terminal 32 to enter patient-generated medical information including easily measured health data (height, weight etc.), allergies, medications, and information that may be duplicated by the records of the databases 22 as recalled by the patient.

A health data repository 30 differs from a personal health record (PHR) to the extent that it also allows importing of clinical medical data from the databases 22. For this purpose, the health data repository 30 may provide for a direct network connection 38 via the internet or other means with the computers 18 of the institutions 10 and 12 which may transfer medical records from the databases 22 using, for example, a common document format such as the Continuity of Care Document (CCD) described by ANSI standard ANSI/HL7 R1-2000, R2-2005 hereby incorporated by reference or the Continuity of Care Record (CCR) described by ASTM CCR standard E2369-05 hereby incorporated by reference.

The goal of the health data repository 30 is to provide for control by a patient of the patient's health record and thereby to assist in preservation of medical records as a patient moves between institutions 10 and 12 through his or her life providing continuity in these records.

Prototype health data repositories 30 of this type are currently being offered by Epic Systems Corporation under the Lucy trademark, by Microsoft Corporation under the HealthVault tradename and by Google Corp. under the tradename Google Health.

The present invention contemplates that the program 33 of the health data repository 30 will give the patients considerable latitude in organizing their medical information in the health data repository 30, both patient-generated and physician-generated. In such systems, the patient-generated and physician-generated data will be collectively referred to as patient-controlled data.

Specifically, such health data repositories 30 may provide one or more of the following features: selective sharing or redaction of portions of physician-generated medical data documents, elimination of the duplicate patient-controlled medical data, selection among conflicting patient-controlled medical data, and editing (including creation) of patient-controlled medical data. The selective sharing feature allows a patient to provide an indication associated with elements of medical data indicating whether the patient wishes to have the elements shared with the institutions 10 and 12. Using this sharing feature, medical data control by the patient may be automatically forwarded to each of the institutions (or automatically transferred by institution request) providing a simple method of updating the multiple institutions 10 and 12 both with patient-generated data and with physician-generated data from the other institution. Documents uploaded by the patient from an institution 10 or 12 may have all or portions of the documents shared so that some portions of the documents are not shared. A functionally similar approach allows redaction of elements of the documents by the patient in the database of the repository so that these records are also removed from access by the patient as well as anyone else accessing the records from the repository.

As data is imported from different institutions or provided by the patient to the health data repository 30, duplications in the data may occur. If the duplicate data is the same, the program 33 of the health data repository 30 may allow the patient to delete redundant data with respect to its display to the patient and/or sharing. Alternatively, if the duplicate data is different, the patient may reconcile the data selecting one data element in favor of the others and deleting or redacting the others. In addition, the health data repository 30 through program 33 may permit the patient to edit the data, changing its value.

Figure 2:
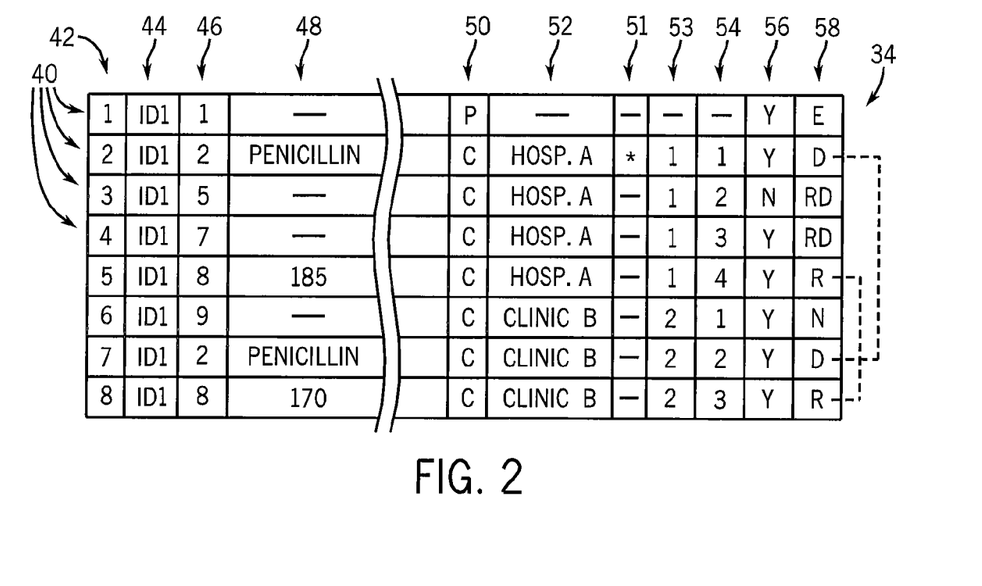
FIG. 2 is a logical representation of a database of the health data repository in collecting healthcare information for a given patient, the database preserving data source, organization, sharing, and editing information.

Referring to FIG. 2, a database 34 of the health data repository 30 may be logically represented tabularly as a set of records 40 each represented by one row of a database 34 with each of the records 40 divided into fields represented by columns of the table. It will be understood that this logical representation embraces a variety of different database organizational structures of types well known in the art, and further that it is a simplification and that an actual database will include different fields and organization.

As shown in FIG. 2, the first field 42 may provide a unique number for each record 40 and a second field 44 may provide for a patient identification, being a unique number or the like identifying a patient from others. The patient identification may provide a link to other information about the patient including name, address, and the like. In this case, the records 40 of the single patient are shown which represents a minimum health data repository 30. Typically, the health data repository 30 will serve multiple patients, and so the patient identification may also link to a username/password for implementing a secure logon to health data repository 30 limiting access to the patient's records 40 by persons other than the patient.

A next field 46 may provide a machine-readable data-type indicating the type of medical data represented by the record 40. The data type of field 46 may be followed by the particular medical data of field 48. For example, the data type of field 46 may be allergy information and the medical data of field 48 may be the allergen.

The present invention contemplates one or more additional fields 50-58 which increase the usability of the data as it is transferred. The first field 50 indicates whether the data was patient-generated (P) or patient-collected (C). As noted above, "patient-collected" data will mean clinical medical data entrusted to the patient and being transferred under the authority or control of the patient, while "patient-generated" data will mean medical information developed by the patient using the patient's own observations or memory. "Patient-collected" data can include data collected from automatic monitoring equipment.

The next field 52 provides an attribution or source for patient-collected data (for example, an identification of a particular hospital or clinic). These two fields can be conflated into one, with a blank entry in field 52, indicating patient-collected data, and all other data being considered patient-generated.

The present invention contemplates that this field can hold not only the name of the institution, but potentially, also the name of the health care professional responsible for the collection of the data either directly or under his or her supervision ("the sourcing physician"). In either case, a field 51 is provided allowing the health care professional responsible for the data to highlight or flag certain records 40 with respect to their importance. This highlighting (shown as an * in FIG. 2) does not change the medical data but like the other information in fields 50-58 serves to characterize the significance or authority of the data. A numeric ranking scale of importance may also be employed.

The next fields 53 and 54 apply to patient-collected data and provide the document structure of the data, field 53 providing a unique document number that will be shared by all data (records) associated with a single document (e.g. CCD, CCR). Field 54 provides unique numbers of each record 40 of that document. The numbers of these fields may be chosen arbitrarily so long as they are unique for each document and for each record 40 within a document.

Field 56 provides a set of sharing codes indicating the patient's preference for sharing of the particular record 40. A given record 40 or data element may be shared (Y) or not shared (N) on a record 40 or element-by-element basis. These sharing codes may be expanded to permit sharing to particular institutions 10 or 12 and not to others.

The field 58 provides an edit code allowing the program 33 to distinguish among a variety of types of modifications of the records 40 or their environment. The edit codes may include, for example: not edited (N), duplicate (D), redacted (RD), reconciled (R), and edited (E). No editing is self-evident and indicates that the medical data of the record 40 controlled by the patient has not been edited by the patient. This may be established, for example, by watermarking techniques (for example using public-key encryption) associated with the record 40 or through a direct downloading of the record 40 to the health data repository 30 under the control of the health data repository 30. Patient-generated data can never be classified as not edited (N) but is always automatically classified as edited (E). Patient-generated data, however, may be attributed to a clinic or the like by the patient using field 54 (such attribution is not shown in FIG. 2).

The edit code of duplicate (D) is used when a record 40 received from an institution 10 or 12 provides duplicate information (identical data type of field 46 and data value of field 48) that is already in the database 34 from another institution 10 or 12 or from the patient. The existence of duplicate records 40 may be noted to the patient during a merging process when that document is received and need not alter or erase data of the record 40 but only indicates that the record 40 is a duplicate and ideally provides pointers to the other records 40 with which duplication exists. This edit code may be used, for example, by the health data repository 30 to prevent the display of redundant data.

In the example of FIG. 2, records 2 and 7 both indicate a penicillin allergy recorded by different institutions 10 and 12 and each may be marked as a duplicate.

The edit code of redacted (RD) may be used to indicate that a portion of a document is missing (deleted or not shared) per records 3 and 4. Note that the edit code of (RD) is attached to non-redacted data, and indicates that other data of the document was redacted. In an alternative embodiment of the invention, multiple edit codes are possible for each record 40, so, for example, records 5 may have the (RD) edit code and the (R) edit code. Or the edit codes may conflate to one edit code as shown.

The edit code of reconciled (R), unlike duplicate, indicates that the patient made a selection among inconsistent records 40 for duplicate data types. For example, record 5 and record 8 may indicate different clinical data values for medical data related to a medical type, for example weight, and the patient may select between these. Again, each reconciled record 40 may preserve a link to the other records 40 with which it was reconciled so that the complete data set can be reconstructed.

Figure 3:
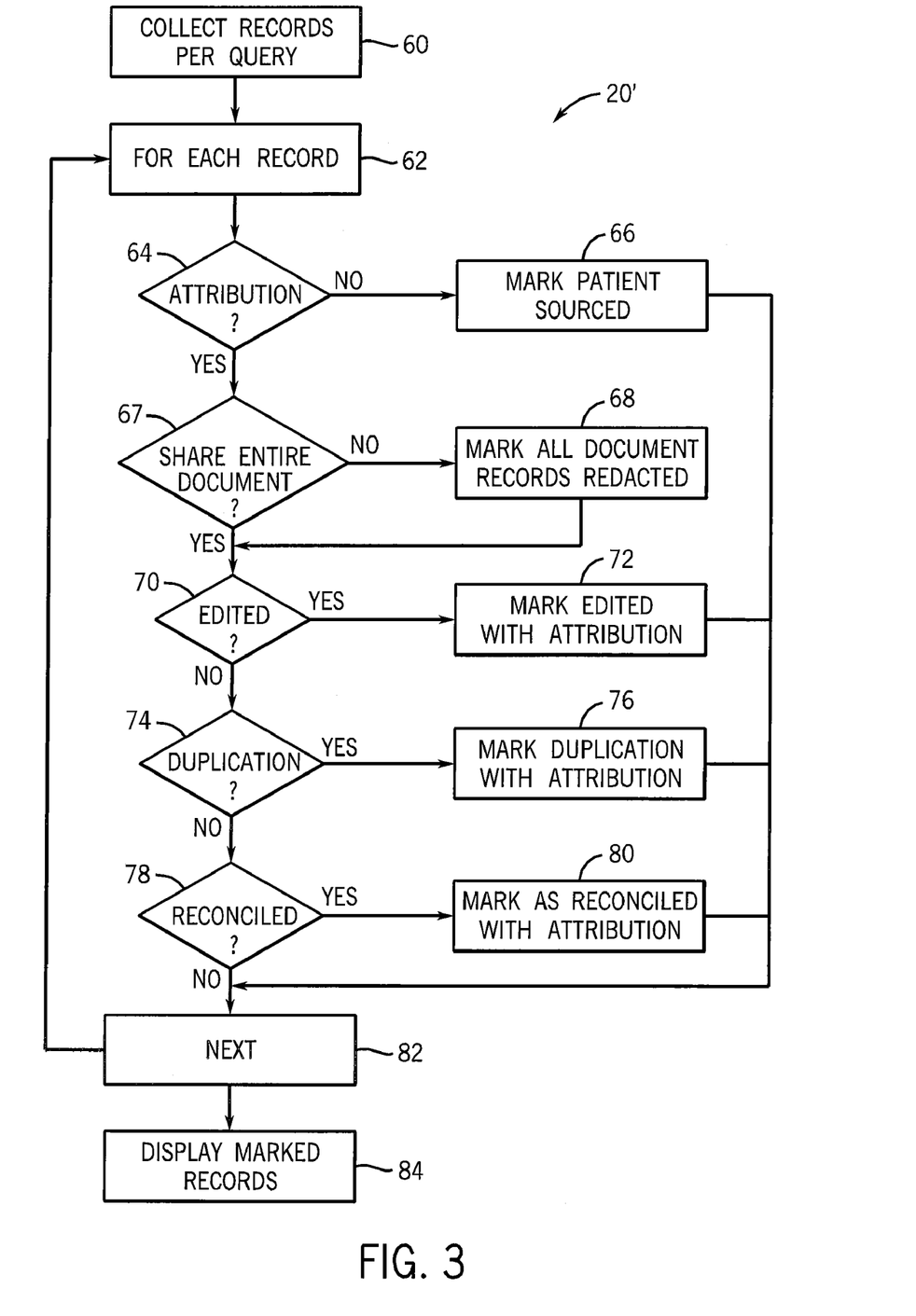
FIG. 3 is a flow chart of a program executed by a clinical record system at the first clinical institution for displaying medical data, including medical data from the health data repository and providing authority indicia for that data.

Referring now to FIG. 3, the database 34 of FIG. 2 allows a sophisticated integration of this data into the clinical medical records of databases 22 by a program 20' being, for example, part of program 20. Using program 20', institution 12, for example, may receive data from a health data repository 30. This receipt of data may be incident with receiving a new patient for care (the patient having a health data repository 30). Alternatively, the receipt of data may occur as part of an ongoing relationship with a patient who uses multiple institutions 10 and 12, the data being transmitted from the health data repository 30 on a regular basis or by request by the patient or the institution 10 or 12. While the data from the health data repository 30 has great value, as noted above, not all of the data has the same authority. Accordingly upon receipt of the data, program 20' undertakes an assessment of the data using all or some of the information from the editing fields 50-58 preserved by the health data repository 30.

This evaluation may be performed per any of the events described above as indicated by decision block 64. For each record 40, as indicated by process block 62, the record 40 may be evaluated to determine whether there is an attribution (field 52) as indicated by decision block 64 or whether the record 40 is patient-generated as recorded by field 50. If there is no attribution or the data is patient-generated, then the record of 40 is marked as patient-generated per process block 66.

If there is an attribution and the record 40 is part of a patient-collected document having other records 40, then at decision block 67 it is determined whether the entire document (that is all of its records 40) is marked for sharing per field 56. If any of the records 40 are not marked for sharing, then at process block 68 all of the records 40 of that document are marked as redacted, indicating that the data is accurate but some, possibly material, medical data may be omitted.

In either case, at succeeding decision block 70, the record 40 is evaluated to determine whether it has been edited. Regardless of its previous attribution, if the document was edited, then at process block 72, the record 40 is marked as edited; however, the attribution that is the source of the document may still be retained. Generally, in the case of patient editing, any marking of the record as important by the sourcing physician is removed.

If the document has not been edited, then the program 20' proceeds to decision block 74 to determine if the particular record 40 has been marked duplicated by the health data repository 30. If so, at process block 76, the record 40 is marked a duplicate and the attribution of the duplicate record 40 is retained providing information to the physician that multiple institutions have validated this particular piece of data. Any marking of either redundant record as "important" by the sourcing physician is preserved and attached to the displayed record.

If the record 40 was not marked as a duplicate, it is examined at decision block 78 to see if it has reconciled data and, if so, at process block 80 the data is marked as reconciled. Optionally, the attributions for the reconciled data may be saved as well as the values of that data. If one of the reconciled records has been marked as "important" by the sourcing physician, this importance may be displayed, provided the unreconciled records is also displayed as will be described below.

This process is repeated per process block 82 in a loop until records 40 from the health data repository 30 are analyzed and marked. The marked data may then be integrated into the database 22 after which the program 20' may proceed to process block 84 to display the records to the physician.

During the display process 84, the marked records from the health data repository 30 may also be in conflict or duplicated with existing clinical records of database 22 at the institution 12. The program 20' may automatically delete or hide duplicate records received from the health data repository 30 in favor of the high authority records of the clinical database 22 and likewise may reconcile any conflicting data to the high authority records of the clinical database 22, optionally with confirmation and possible override by the physician.

The display process 84 may permit selecting among the types of markings that will be displayed. For example, the "redacted" marks may be suppressed if the physician is not interested in this level of detail.

Figure 4:
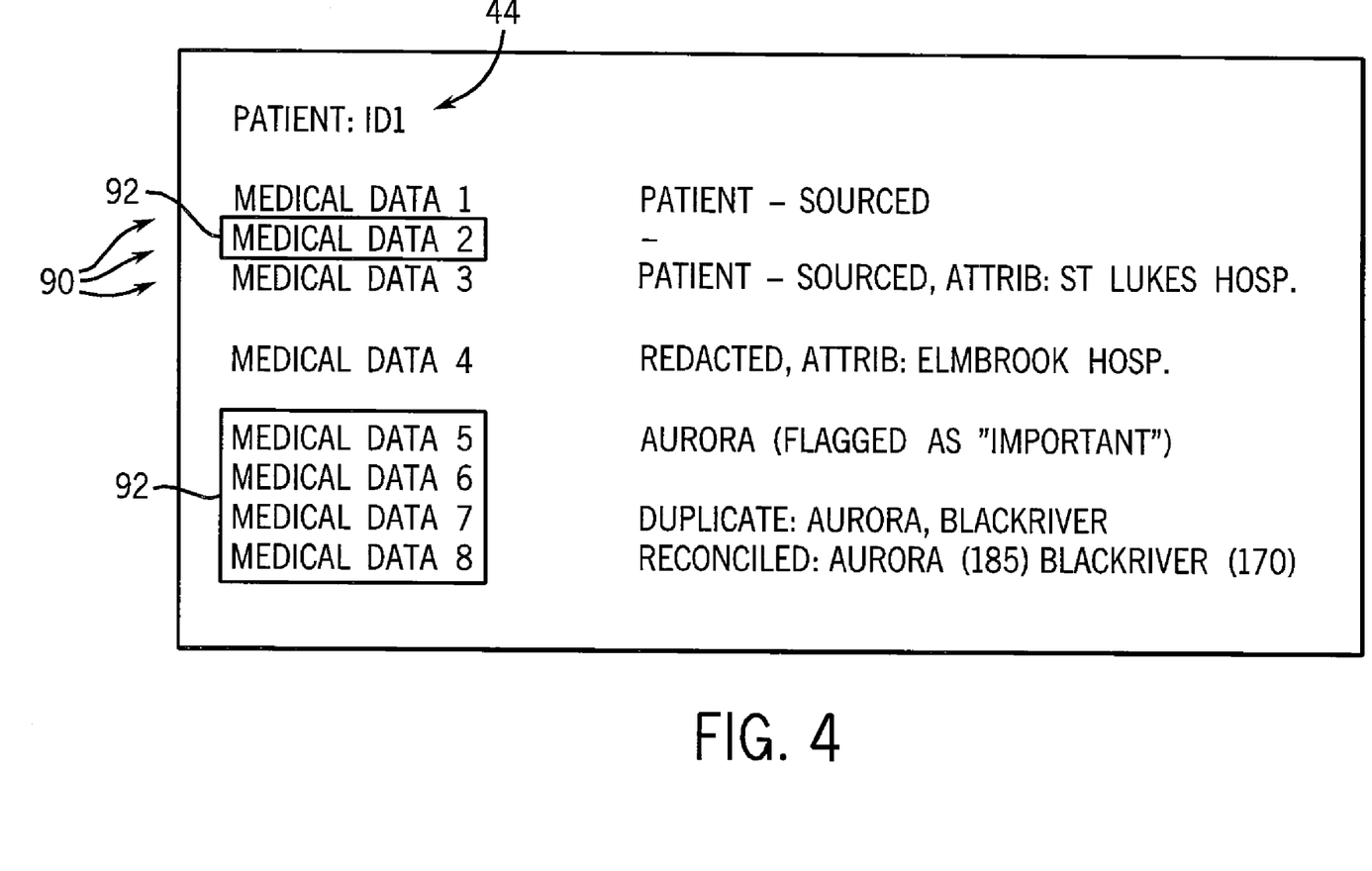
FIG. 4 is a simplified representation of a display of the data as presented to a physician marked by authority levels and using an authority threshold.

Referring now to FIG. 4, a typical display for such a system would display the patient name as deduced from the patient ID of field 44 together with selected medical data 90 culled from the records 40 of the patient, for example, selected from the database 22 through a database query executed by the physician or automatically being part of a predefined form. Different display modes 92 (for example highlighting or color) may optionally be applied to the data 90 to indicate qualitatively the authority of the data. Preferably, the highest quality medical data may be highlighted according to a threshold that may be programmed by the institution 12 separating among the various levels of authority ranked generally as follows:

| Level of Authority | Source Medical Data |
| --- | --- |
| 1* | Data with attribution, not edited or redacted, but duplicated by multiple institutions, flagged by sourcing physician as important |
| 1 | Data with attribution, not edited or redacted, but duplicated by multiple institutions |
| 2 | Data with attribution, not edited or redacted and not duplicated |
| 3 | Data with attribution, not edited, but reconciled |
| 4 | Data with attribution, not edited but some data redacted |
| 5 | Data with attribution, edited |
| 6 | Patient-generated, edited data |

For example, data with authority values 1-3 may be highlighted as high-quality data for the physician. Alternatively, the display of records may be controlled by their authority level with a physician selecting by filter settings, a desired level of authority of all displayed records. In this case, for example, the physician may set the authority level to level 3 or below (levels 1-3) in which case data associated with levels 4-6 would not be displayed. Similarly, individual levels may be suppressed, for example, level 5, while allowing level 6.

Each element of medical data derived from a record may be further labeled with a label providing additional physician guidance. For example, authority level 5 data (shown in FIG. 4 as "medical data 1") may be marked with the text "patient-generated" or a similar abbreviation or symbol. Similarly as shown with "medical data 3", data with an attribution (e.g. institution 10 or 12) but edited will be indicated as patient-generated yet the attribution retained. This allows the physician to confirm the data with the institution if desired and preserves the attribution information even though it may not provide self-authentication.

As indicated with "medical data 4", un-edited data from an institution where the data is part of a document having some data removed or unshared, may be labeled "redacted" and the institution attribution provided. Data from the clinical database 22 of institution 12 itself, for example, "medical data 2" may be highlighted with no attribution indicating that it is internal data of the highest quality.

High quality data from another institution being part of a document that has neither been edited nor redacted, as indicated by "medical data 5" and "medical data 7" and the data that has been reconciled with other high-authority data from other institutions that has neither been edited nor redacted, shown by "medical data 8", may be displayed as high-value with the rejected values and their attributions displayed. As shown by "medical data 5" any data marked as important by a physician in the sourcing institution may be marked as such.

Duplicate data may select the data of the highest authority to display. Reconciled data may further show the attributions together with the conflicting data.

The present invention thus provides a method for a physician to obtain the very best data that has been collected for his or her patient while also understanding the chain of custody of that data to the extent that it can affect the data's authority and the physician's decisions. Note that the authority provided by the present invention necessarily varies in importance depending on the type of data and the amount of reconciliation. For example, inconsistent data related to the patient's weight may be easily understood (within certain ranges) as being of relatively low significance. Further, some types of clinical information that are patient-generated or sourced from a redacted or edited document may nevertheless be perfectly acceptable because there is little likelihood of a serious mistake or missing data being materially relevant to the data provided. Other data may be more sensitive to any editing or redaction and the redaction itself may be significant to the physician in certain cases even when the data itself has not been shared.

It will be understood that the term physician as used herein includes any authorized health care professional using the clinical records system.

It is specifically intended that the present invention not be limited to the embodiments and illustrations contained herein and the invention should be understood to include modified forms of those embodiments including portions of the embodiments and combinations of elements of different embodiments as come within the scope of the following claims.

We claim:

1. A health record system comprising:
a first clinical record system associated with a first medical institution comprising at least one computer communicating with a set of data terminals and a first database and executing a first stored program to collect, organize, and display physician-generated medical data for given patients, the first clinical record system including an authentication protocol limiting access by non-healthcare professionals;
a medical record repository comprising at least one computer communicating with a set of data terminals and a repository database and executing a repository program to collect, organize, and display medical data controlled by given patients, the medical record repository including an authentication protocol limiting access by others than the given patients, the repository program operating to:
(a) accept into the repository database patient-generated medical data from a given patient;
(b) accept into the repository database patient-collected medical data from a second clinical record system of a second medical institution in a manner to be separately identified from the patient-generated data; and
(c) respond to authorization by the given patient to transmit at least some of the patient-generated data and patient-collected data to the first clinical record system;
wherein the first stored program further operates to provide a display output providing medical data for the given patient visually linked to a visual indication of an authority of the data based on its identification as physician-generated having a high level of authority, patient-generated having a low level of authority, or patient-collected having a medium level of authority, wherein the display output further displays a numerical ranking indicating the level of authority associated with the medical data,
further wherein the first stored program is configured to identify data as physician-generated where the data has not been collected or generated by a patient and where the data was not received at the first clinical record system in the transmittal of the patient-generated data and patient collected data transmitted from the medical record repository.

2. The health record system of claim 1 wherein the repository program further stores an identification of the second medical institution.

3. The health record system of claim 2 wherein the visual indication of authority indicates the second health institution.

4. The health record system of claim 1 wherein the repository program further stores an indication of the importance of at least one record as assigned by a health care professional of the second medical institution.

5. The health record system of claim 4 wherein the display output provides medical data for the given patient visually linked to a visual indication of an importance of the data assigned by a health care professional of the second medical institution.

6. The health record system of claim 1 wherein the medical data has a data type related to a medical character of the data and independent of a source of the data and the first stored program further operates to display physician-generated, patient-generated and patient-collected data sorted according to data types, so that similar data types are proximate to each other in the display.

7. The health record system of claim 1 wherein the first stored program may further receive authority filter parameters from the physician to suppress the display of medical data based on its identification as physician-generated, patient-generated, or patient-collected.

8. The health record system of claim 1 wherein the first stored program may further receive authority filter parameters from the physician to suppress the display of selected visual indications of authority.

9. The health record system of claim 1 wherein the repository program accepts health record documents from the second health institution comprised of multiple medical data and allows the given patient to selectively authorize a subset of the medical data of the document for transmission to the first clinical record system,
wherein the repository program separately identifies medical data associated with a document in which some medical data was not authorized for transmission to the first clinical record system from medical data associated with a document in which all medical data was authorized for transmission to the first clinical record system.

10. The health record system of claim 1 wherein the repository program allows editing of the patient-collected medical data by the given patient and wherein the repository program identifies such edited medical data in a manner to be separately identified from medical data unedited by the given patient.

11. The health record system of claim 10 wherein patient-collected data edited by the given patient is identified as patient-generated data by the repository program.

12. The health record system of claim 1 wherein the repository program accepts health record documents of medical data from the second health institution and evaluates a digital watermark in the documents to ensure the documents have not been edited after release by the second health institution before identifying them as patient-collected data.

13. The health record system of claim 1 wherein the repository program communicates electronically directly with the second health institution to obtain patient-collected data.

14. The health record system of claim 1 wherein the repository program communicates with the first program to provide a display output of the physician-generated data for the given patient to the give patient.

15. The health record system of claim 1 wherein the repository program further operates to:
(d) accept into the repository database patient-collected medical data from the first clinical record system in a manner to be separately identified from the patient-generated data; and
(e) respond to authorization by the given patient to transmit at least some of the patient-generated data and patient-collected data to the second clinical record system.

16. The health record system of claim 1 wherein the repository program further operates to:
(d) respond to authorization by the given patient to transmit at least some of the patient-generated data to the second clinical record system.

17. A health record system comprising:
a first clinical record system associated with a first medical institution comprising at least one computer communicating with a set of data terminals and a first database and executing a first stored program to collect, organize, and display physician-controlled medical data for given patients, the first clinical record system including an authentication protocol limiting access by non-healthcare professionals;
a medical record repository comprising at least one computer communicating with a set of data terminals and a repository database and executing a repository program to collect, organize, and display medical data controlled by given patients, the medical record repository including an authentication protocol limiting access by others than the given patients, the repository program operating to:
(a) accept into the repository database patient-generated medical data from a given patient;
(b) accept into the repository database patient-collected medical data from a second clinical record system of a second medical institution in a manner to be separately identified from the patient-generated data; and
(c) respond to authorization by the given patient to transmit patient controlled medical data, including at least some of the patient-generated data and patient-collected data, to the first clinical record system;
wherein the first stored program is configured to receive medical data directly from the second clinical record system of a second medical institution in a manner to be identified as physician-controlled data, and
wherein the first stored program further operates to provide a display output providing medical data for the given patient visually linked to a visual indication of an authority of the data based on its identification as physician-controlled medical data having a high level of authority, patient-generated having a low level of authority, or patient-collected having a medium level of authority,
further wherein the display output displays a numerical ranking indicating the level of authority associated with the medical data.

* * * * *